United States Patent [19]

Tabor et al.

[11] Patent Number: 4,547,367

[45] Date of Patent: Oct. 15, 1985

[54] HEPATITIS B CORE ANTIGEN VACCINE

[75] Inventors: Edward Tabor, Rockville; Robert J. Gerety, Potomac, both of Md.

[73] Assignee: The United States of America as represented by the Department of Health and Human Services, Washington, D.C.

[21] Appl. No.: 563,369

[22] Filed: Dec. 20, 1983

[51] Int. Cl.⁴ .................................................. A61K 39/29
[52] U.S. Cl. ................................... 424/89; 435/235
[58] Field of Search ............................................. 424/89

[56] References Cited

U.S. PATENT DOCUMENTS 4,100,267 7/1978 Shaw ........................................ 424/1
4,102,996 7/1978 McAleer et al. ....................... 424/89

OTHER PUBLICATIONS

Tabor et al., Lancet, Jan. 21, 1984, p. 172.
Tabor et al., Transfusion, 21(3), May/Jun. 1981, pp. 366-371.
Tabor et al., J. Med. Virol., 6:91-99, (1980).
Neurath et al., J. Gen. Virol., 42:645-649, (1979).
Hoofnagle, N. Eng. J. Med., 298(25):1379-1383, Jun. 22, 1978.
Purcell et al., Am. J. Clin. Pathol., Jul. 1978, pp. 159-169.
Hansson, J. Clin. Microbiol., 6(3):209-211, Sep. 1977.
Tabor et al., J. Immunol., 117(5), (Part 2): 2038-2040, Nov. 1976.
Hoofnagle, Am. J. Med. Sci., 270(1):179-187, (1975).
Hoofnagle, Develop. Biol. Stand., 30:175-185, (1975).
Krugman, Develop. Biol. Stand., 30:363-367, (1975).
Krugman, N. Engl. J. Med., 290:1331-1335, Jun. 13, 1974.
Barker et al., Adv. Int. Med., 23:327-351, (1976).
Shaw et al., Journal of Virology, 12:1598, (1973).
Hoofnagle et al., The New England Journal of Medicine, 290:1336, (1974).
Hoofnagle et al., Lancet, 2:869, (1973).
Barker et al., J. of Virology, 14:1552, (1974).

Primary Examiner—Shep K. Rose
Attorney, Agent, or Firm—John S. Roberts, Jr.

[57] ABSTRACT

Disclosed is a vaccine against hepatitis B virus (HBV) using purified hepatitis B core antigen (HBcAg). Chimpanzees immunized with the vaccine were protected against hepatitis B.

4 Claims, No Drawings

HEPATITIS B CORE ANTIGEN VACCINE

BACKGROUND

The discovery of hepatitis B surface antigen (HBsAg, Australian antigen, or hepatitis-associated antigen) represented a major scientific breakthrough in the characterization and treatment of hepatitis B virus (HBV). The development of a HBV vaccine using HBsAg protected against infection by HBV in most cases but not all. In the early 1970's a second antibody, distinct from anti-HBs, was discovered in response to HBV infection. This second antibody, anti-HBc (anti-core), is directed against the hepatitis B core antigen (HBcAg), located on the internal component of the Dane particle, the intact hepatitis B virus and the core antigen particles found in the liver during chronic infection. However, no material suitable for use as a vaccine has been developed using the inner component, HBcAg. The present invention discloses the preparation of a vaccine against HBV using purified hepatitis B core antigen. This vaccine has been tested in chimpanzees, protecting them against HBV infection. All hepatitis B vaccines shown to be effective in chimpanzees have also been effective in humans.

UTILITY STATEMENT

The vaccine of this invention is useful either alone or as combination vaccines (i.e., vaccines prepared from both surface and core antigens). It is expected that these vaccines will provide both longer protection and more effective protection than the existing vaccine (made solely from the surface antigen). Of greatest importance, a combination vaccine is particularly needed for dialysis patients, a principle group of recipients of the vaccine, and for whom the existing vaccines are relatively ineffective.

Furthermore, the existing vaccines are potentially more harmful than the vaccine of the present invention. In producing synthetic hepatitis vaccines by recombinant DNA techniques, the code for a surface antigen is located proximally to an area on the virus genome called area X. Such closeness to an area with an unknown gene product may produce impurities in the vaccine which may result in harmful consequences. The development of a core antigen-based vaccine obviates this potential harm.

SUMMARY OF THE INVENTION

The present invention provides a new vaccine against hepatitis B virus using purified hepatitis B core antigen, a well-characterized antigen associated with the 27 nm core of the hepatitis B virus. The preferred method of obtaining the core antigen is by differential centrifugation of liver tissue or serum taken from hepatitis B infected humans or chimpanzees. Alternatively, the core antigen may be obtained from clones of prokaryotic or eukaryotic cells containing the gene for the core antigen integrated in their own genome.

The core antigen may be purified by any means suitable—the preferred method of the present invention is differential centrifugation. The purity of a core antigen preparation is confirmed by immune electron microscopy and radioimmunoassay.

Other aspects and advantages of the present invention will be apparent upon consideration of the following specific disclosure and examples.

MATERIAL INFORMATION DISCLOSURE

U.S. Pat. 4,100,267 (Shaw) and Shaw et al, *Journal of Virology*, vol. 12, p. 1598 (1973), detail one method of producing hepatitis B core antigen and antibody. The serum developed by Shaw, from A-2 plaque virus, is not a vaccine.

U.S. Pat. 4,102,996 (McAleer et al) discloses a method of preparing HBcAg from HBV ("Dane particles") from plasma and a method for increasing the HBcAb (anti-HBc) titer in individuals already recovered from HBV infections to produce an immune-globulin. Therefore, this disclosure is not a vaccine.

Hoofnagle et al, *The New England Journal of Medicine*, vol. 290, p. 1336 (1974); Hoofnagle et al, Lancet, vol. 2, p. 869 (1973); and Barker et al, *J. of Virology*, vol. 14, p. 1552 (1974) all disclose preliminary discoveries, experiments, and background dealing with HBcAg. The present vaccine was ultimately developed from these early discoveries.

SPECIFIC DISCLOSURE

The HBcAg disclosed in the following examples is purified by ultra-centrifugation. The liver of a chimpanzee who died from pneumonia during experimentally induced HBV infection is removed and stored at $-20°$ C. Liver sections are examined by electron microscopy to confirm the presence of 27-nm intranuclear core particles. Liver (80g) is suspended in 320 ml hypotonic (0.45%) saline and homogenized in a blender. The 20% (wt/vol) homogenate is clarified by centrifugation at 2,500 RPM for 30 minutes. The supernatant fluid is then centrifuged at 25,000 RPM for 2 hours in an ultracentrifuge. The resulting pellet is resuspended in distilled water, followed by high speed centrifugation (25,000 RPM for 2 hrs). The pellet is then resuspended in 35 ml of distilled water and clarified again by centrifugation at 2,500 RPM for 30 minutes. To further purify the supernatant, it is layered onto a continuous CsCl gradient (density 1.2 to 1.5 g/ml). The gradient mixture is then centrifuged at 22,000 RPM for 16 min. in an ultra-centrifuge. Fractions are collected dropwise from the bottom of the tube in approximately 1 ml amounts. Each fraction is assayed for HBsAg by radioimmunoassay and for HBcAg by complement fixation and examined for virus-like particles under the electron microscope. Fractions containing typical 27-nm core particles are dialyzed for 1 to 3 days against phosphate-buffered saline and used to immunize susceptible species, and for immune electron microscopic studies. Susceptible species, used here and in the claims, are those species susceptible to hepatitis B virus, including humans, chimpanzees, and gibbons.

EXAMPLES

Example 1 illustrates the protective ability of the vaccines and the suitability for use in chimpanzees. For the purposes of this invention, a chimpanzee is considered a surrogate human, permitting controlled evaluation in a protected environment. Serologic and cell-mediated immune responses to HBV antigens have been shown to be identical in chimpanzees and humans. Examples 2-5 describe some of the protocols involved in administration of the vaccine and are exemplary of how the vaccine of this invention may be applied.

EXAMPLE 1

Hepatitis B core antigen (HBcAg) was purified from the liver of a chimpanzee infected with HBV, by ultracentrifugation and CsCl density gradient centrifugation. Aliquots containing 50 ug of HBcAg each were used to immunize susceptible chimpanzees, with or without an adjuvant. Immunization was performed subcutaneously at 0, 2, and 6 weeks. Both immunized chimpanzees made anti-HBc. Each chimpanzee was challenged at 10 weeks using an HBV inoculum of documented infectivity ($10^3$ infectious doses per one ml inoculum, as documented in previous chimpanzee titration studies). Both chimpanzees were protected against HBV infection. One had anti-HBs detectable beginning 18 weeks after challenge. Neither chimpanzee had detectable HBsAg. Serum aminotransferase levels remained in the pre-inoculation range, and no evidence of acute hepatitis was detected in liver biopsy specimens. Thus, immunization resulted in protection against hepatitis B in both chimpanzees; one chimpanzee was protected against both infection and disease, and the other had seroconversion without disease.

EXAMPLE 2

Three healthy adult humans are inoculated with three doses of HBcAg subcutaneously at zero, one, and six months. Inoculations are 10 ug per dose for the first adult, 50 ug per dose for the second adult, and 100 ug per dose for the third adult. Peak titers of anti-HBc are reached by seven months after onset of the study, and are 1:10, 1:500, and 1:1,000, respectively, accompanied by evidence of cell-mediated immunity to HBcAg. No other serologic markers of HBV are detected.

EXAMPLE 3

Ten new surgical interns are immunized with 20 ug of HBsAg and 50 ug of HBcAg subcutaneously at zero, one, and six months. All develop anti-HBs and anti-HBc; none have HBsAg in any serum sample. Testing of monthly serum samples during the succeeding 18 months reveal that all are protected against hepatitis B infection despite daily exposure to sources of the virus.

EXAMPLE 4

During a large-scale vaccination program for hepatitis B using an HBsAg vaccine, ten vaccine recipients are identified who produce no detectable anti-HBs despite three vaccine doses. These ten are subsequently immunized subcutaneously with three doses of 50 ug of HBcAg each at zero, one, and six months. Nine of the ten vaccinees develop anti-HBc, in the absence of other hepatitis B serologic markers. These nine do not develop hepatitis B during subsequent evaluation.

EXAMPLE 5

Three infants born to HBsAg-positive mothers are immunized at birth, one month, and six months of age with 20 ug of HBsAg and 50 ug of HBcAg. All three develop high titers of anti-HBs and anti-HBc. No HBsAg is detected during 18 months of follow-up.

We claim:

1. A method of protecting chimpanzees by administering a vaccine prepared by a process which comprises centrifuging and isolating HBcAg from the liver of an infected chimpanzee, mixing said HBcAg with a suitable adjuvant to form a vaccine and injecting said vaccine into the chimpanzee.

2. A method of protecting chimpanzees from hepatitis B virus which comprises subcutaneously injecting said chimpanzees with a vaccine which is a mixture of HBcAg and HBsAg.

3. The method of claim 2 in which HBcAg is present in the amount of approximately 50 ug and the HBsAg is present in the amount of approximately 20 ug.

4. A method of protecting susceptible species against hepatitis B by administering a vaccine prepared by the process of claim 1.

* * * * *